(12) United States Patent
Berchowitz

(10) Patent No.: US 9,587,873 B2
(45) Date of Patent: Mar. 7, 2017

(54) ENERGY EFFICIENT BIOLOGICAL FREEZER WITH VIAL MANAGEMENT SYSTEM

(71) Applicant: Global Cooling, Inc., Athens, OH (US)

(72) Inventor: David M. Berchowitz, Athens, OH (US)

(73) Assignee: Global Cooling, Inc., Athens, OH (US)

( * ) Notice: Subject to any disclaimer, the term of this patent is extended or adjusted under 35 U.S.C. 154(b) by 212 days.

(21) Appl. No.: 13/778,468

(22) Filed: Feb. 27, 2013

(65) Prior Publication Data

US 2013/0255283 A1 Oct. 3, 2013

Related U.S. Application Data

(60) Provisional application No. 61/616,021, filed on Mar. 27, 2012.

(51) Int. Cl.
| | |
|---|---|
| *F25D 11/00* | (2006.01) |
| *F25B 25/00* | (2006.01) |
| *F25D 11/04* | (2006.01) |
| *A01N 1/02* | (2006.01) |
| *F25B 9/14* | (2006.01) |
| *F25B 23/00* | (2006.01) |
| *F25D 25/04* | (2006.01) |

(52) U.S. Cl.
CPC ............ *F25D 11/00* (2013.01); *A01N 1/0252* (2013.01); *F25B 25/005* (2013.01); *F25D 11/04* (2013.01); *F25B 9/14* (2013.01); *F25B 23/006* (2013.01); *F25D 25/04* (2013.01)

(58) Field of Classification Search
CPC .......... F25D 11/00; F25D 11/04; F25D 25/00; F25D 25/04; F25B 9/14; A01N 1/0252; G01N 2035/0455
See application file for complete search history.

(56) References Cited

U.S. PATENT DOCUMENTS

| | | | | |
|---|---|---|---|---|
| 2,496,304 A | * | 2/1950 | Muffly | F25D 17/02 194/277 |
| 3,296,815 A | | 1/1967 | White | |
| 5,056,332 A | * | 10/1991 | Tajima | F25D 17/065 312/116 |
| 5,191,267 A | * | 3/1993 | Machacek | 318/67 |

(Continued)

OTHER PUBLICATIONS

TTP Labtech Arktic system. http://www.ttplabtech.com/new/arktic.html.

*Primary Examiner* — Ryan J Walters
*Assistant Examiner* — Christopher R Zerphey
(74) *Attorney, Agent, or Firm* — Frank H. Foster; Kremblas & Foster

(57) ABSTRACT

An automated, ultra-low temperature freezer having multiple structural features that reduce heat transfer into the freezer, protect its internal mechanical devices against low temperature mechanical binding of their movements, allow defrosting and autoclaving as a result of only minimal changes to the conventional $CO_2$ emergency backup system. A group of freezers are arranged so they can simultaneously provide an HVAC function. A vial management system allows biological samples or vials to be automatically placed in and recovered from the freezer and associates the temperature history with each sample or vial that it was subjected to during its storage.

12 Claims, 11 Drawing Sheets

(56) References Cited

U.S. PATENT DOCUMENTS

| | | | |
|---|---|---|---|
| 5,233,844 A * | 8/1993 | Knippscheer et al. | 62/440 |
| 5,315,840 A | 5/1994 | Viegas et al. | |
| 5,664,435 A * | 9/1997 | Bassuk | A47F 3/0404 |
| | | | 62/381 |
| 6,129,428 A | 10/2000 | Helwig et al. | |
| 7,861,540 B2 | 1/2011 | Cloutier et al. | |
| 8,176,747 B2 | 5/2012 | Howard et al. | |
| 2002/0023444 A1 | 2/2002 | Felder et al. | |
| 2002/0134088 A1 | 9/2002 | Rudick et al. | |
| 2004/0154322 A1 | 8/2004 | Felder et al. | |
| 2005/0081558 A1* | 4/2005 | Yoshida | 62/457.9 |
| 2006/0053825 A1 | 3/2006 | Owen et al. | |
| 2009/0188272 A1* | 7/2009 | Cloutier et al. | 62/378 |
| 2009/0266085 A1* | 10/2009 | Goodwin et al. | 62/3.2 |
| 2013/0199232 A1* | 8/2013 | Natarajan et al. | 62/335 |

* cited by examiner

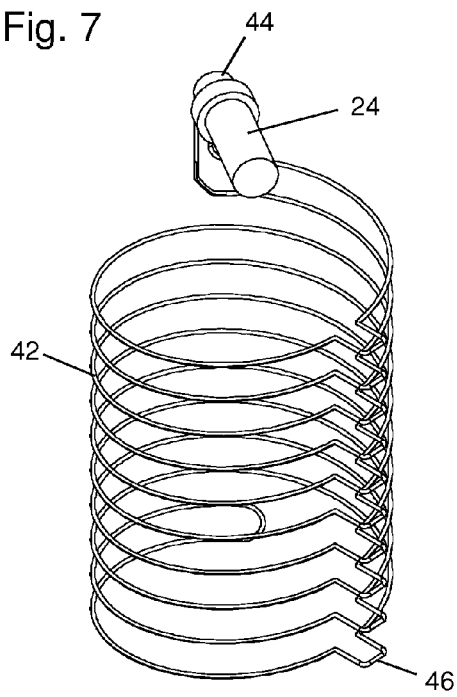
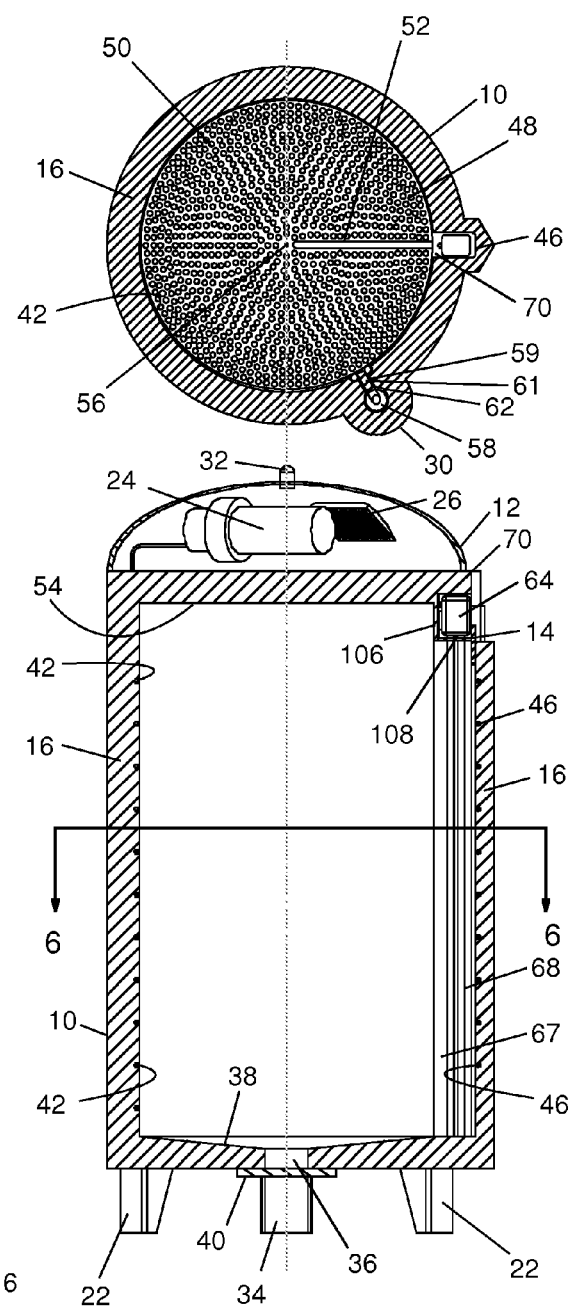

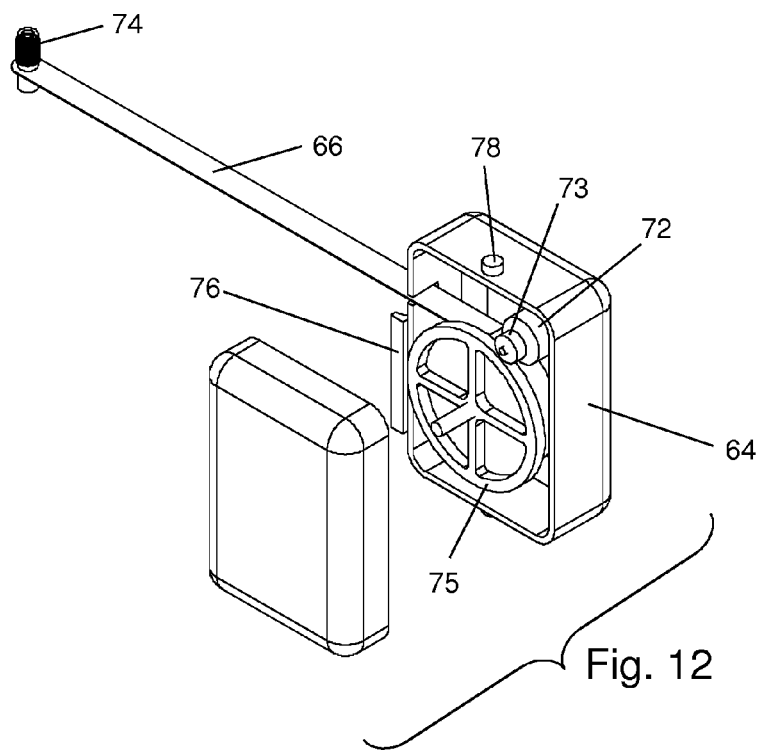
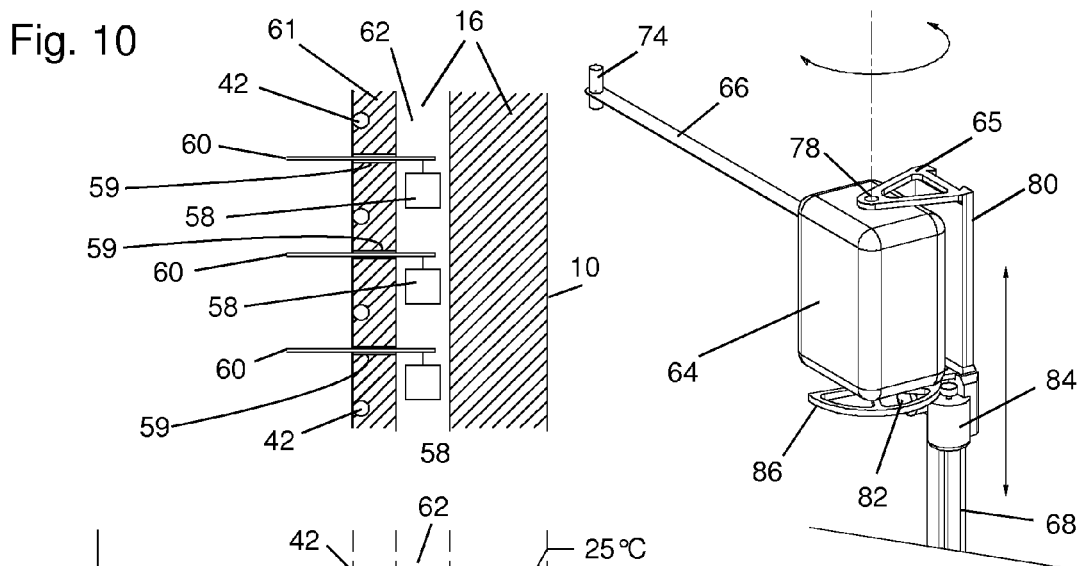
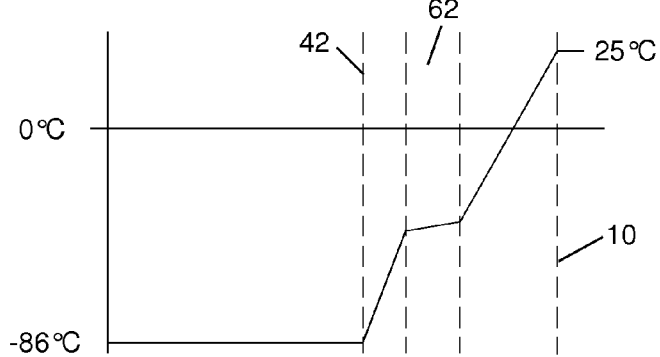

Fig. 14
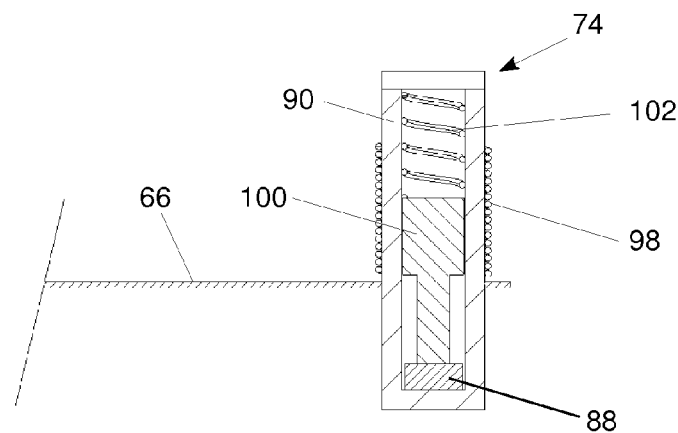
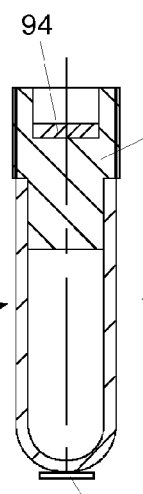
Fig. 15
Fig. 16
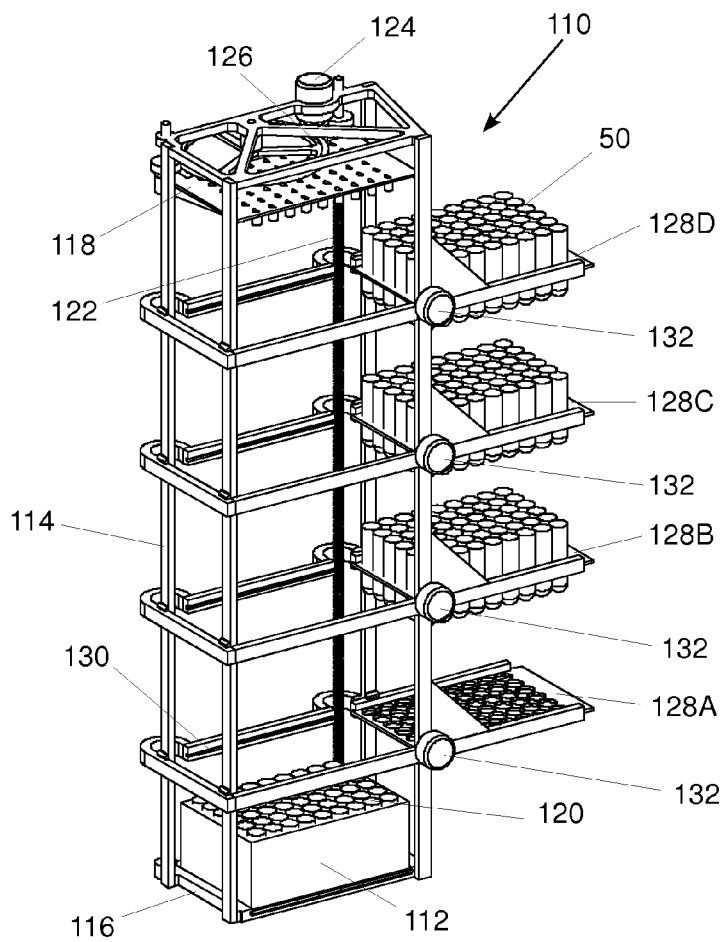

ENERGY EFFICIENT BIOLOGICAL FREEZER WITH VIAL MANAGEMENT SYSTEM

BACKGROUND OF THE INVENTION

Technical Field

This invention relates generally to ultra-low temperature freezers used in biological and pharmaceutical industries for storing biological samples. More particularly, the invention relates to improving the energy consumption of such ultra-low temperature freezers and to more efficiently use the energy that they do consume. Energy consumption is improved by providing a compact storage structure for biological sample containers and by reducing heat transfer by conduction and convection into the freezer including heat transfer during sample storage or retrieval operations. Simple defrosting and autoclaving functions are provided. The freezer heat pumping equipment is also adapted to provide HVAC functions for the room that houses multiple operating freezers thereby reducing or eliminating the cost of an HVAC system.

Background Art

Universally, large biological freezers use cascade systems to provide the cooling mechanism for obtaining low temperatures. Cascade systems are prone to failure due to oil migration, are inefficient leading to high energy costs and modulate their temperatures by switching the cooling system on and off. Reliability in this application is non-negotiable and consequently backup systems are in wide use. The inefficiency of cascade systems leads to high operating costs due to the consumption of electrical energy. For example, an 800 liter cascade freezer consumes up to 13,000 kWh per year and in many cases, even more than this. Facilities may have a number of freezers and total operating costs including the HVAC costs that are necessary to remove the heat generated from the inefficient systems, can amount to considerable expenses. Furthermore, biological freezers store samples in vials that are collected into boxes that are then placed into racks that are finally placed into an ultra-low temperature (ULT) freezer. Often times, these sample vials are hand marked and manually placed into the ULT freezer. This leads to frequent door openings, which affects temperature stability and access error due to the often-large number of sample vials that may be stored in a freezer and the manual nature of the processes of storing and retrieving them and of recording their location. Recently the company Hamilton Storage Technologies, Inc. has brought their knowledge of automation to the problem and has developed a system for auto-inventorying of sample vials in ULT freezers. Though this is a huge step forward, it is also a cumbersome system that consumes a lot of floor space thus increasing the already high energy usage per sample vial and furthermore, by placing most of the robotic movers within the cold space, reliability and life are compromised.

Therefore, an ideal biological sample vial storage and management system would have:

a. Extremely high reliability and fidelity of temperature;
b. Maximum use of facility space and minimum energy consumption in order to reduce storage costs;
c. An automatic storage and retrieval system;
d. An automatic database available on a personal computer or the Internet that tracks the sample vials and their temperature history along with associative data arbitrary or specific;
e. The system should be scalable. Meaning that units should stack as closely as possible and share the vial storage management system.

BRIEF SUMMARY OF THE INVENTION

A freezer of the invention can include a stack of trays driven in rotation by motors that are within the freezer but are maintained at a warmer temperature than stored samples in the freezer by positioning the motors in an interior cavity in the surrounding insulation between a thermosiphon along the interior walls and the exterior of the freezer. An automatically controlled trolley robot, for sample container insertion and retrieval, moves vertically along a plenum in the interior of the freezer and is parked in a garage when inactive for maintaining the trolley robot at a warmer temperature. The trolley robot arrangement also allows a freezer access portal and its door to be very small in order to substantially reduce heat transfer into the freezer. The interior of the freezer can be defrosted and/or autoclaved by modification according to the invention of a conventional $CO_2$ emergency backup system. The invention allows a group of ULT freezers to be simultaneously used for an HVAC function. A vial management system allows biological samples or vials to be automatically placed-in and recovered-from the freezer and associates the temperature history with each sample or vial that it was subjected to during its storage.

BRIEF DESCRIPTION OF THE SEVERAL VIEWS OF THE DRAWINGS

FIG. 4 is a view in vertical, axial section of an embodiment of the invention.

FIG. 5. is a view in vertical, axial section of an embodiment of the invention.

FIG. 6 is a view in horizontal section taken substantially along the line 6-6 of FIG. 5.

FIG. 7 is a view in perspective of a thermosiphon that is a component of some embodiments of the invention.

FIG. 10 is a diagrammatic view in elevation illustrating some of the tray rotational drives and their placement in the sidewall insulation of a freezer.

FIG. 11 is a graph illustrating the temperature gradient from the exterior of a freezer, through the space containing the drive motors for rotating the trays, and to the interior of the freezer.

FIG. 12 is an exploded view in perspective of a trolley robot of the invention with a part of its casing removed to expose its interior structures.

FIG. 13 is a view in perspective of the trolley robot of FIG. 12 with its carriage and tracks for guiding its vertical movement.

FIG. 14 is a view in vertical, axial section of a picker for grasping vials for transportation to and from the interior of the freezer.

FIG. 15 is a view in vertical, axial section of an example of a sample vial stored in the freezer.

FIG. 16 is a view in perspective of an embodiment of a tray handler mechanism that may be used with the invention.

Figure 1:
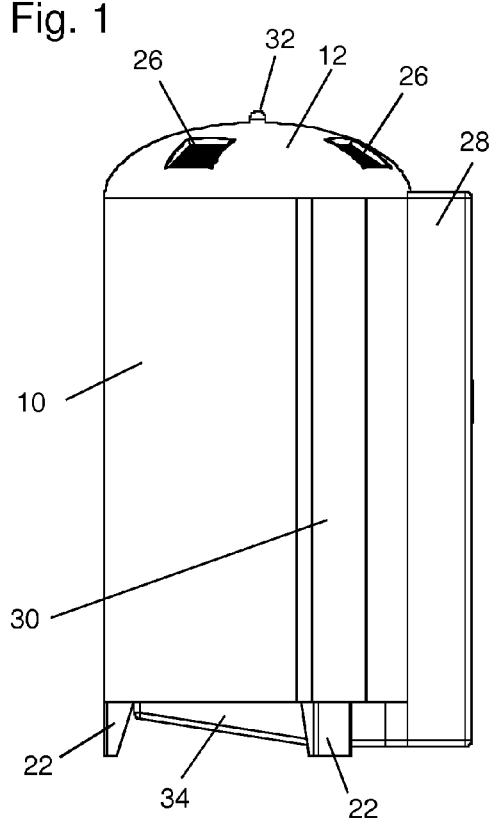
FIG. 1 is a view in side elevation of a freezer embodying the invention.

In describing the preferred embodiment of the invention which is illustrated in the drawings, specific terminology will be resorted to for the sake of clarity. However, it is not intended that the invention be limited to the specific term so selected and it is to be understood that each specific term includes all technical equivalents which operate in a similar manner to accomplish a similar purpose.

DETAILED DESCRIPTION OF THE INVENTION

A part of this invention is concerned with the minimization of consumed energy. In order to effectively achieve this part of the goal, the heat leak into the ULT freezer cabinets must be minimized. There are three means by which heat enters into the ULT freezer cabinets:

a. Heat conducted through the walls. This is proportional to the surface area of the walls and is usually about two thirds of the heat leak.

b. Heat conducted through the gasket area of the door. The presence of the door compromises the thermal properties of the cabinet because the gasket is not able to have the high insulative characteristics of the walls. Typically, the gasket accounts for one third of the heat leak.

c. Door openings. With each door opening, much of the cold interior space is warmed. Inner doors are often employed to ameliorate this problem but not with great success. Door openings therefore increase the heat load and subject sample vials to higher ambient temperatures, even if only for a short time.

Heat leakage has been kept to a minimum by constructing the cabinet in a cylindrical form with a small door that is only large enough to allow storage and retrieval of the vials, or other storage containers. A cylinder has less surface area than an equivalent rectangular cabinet and the small size of a door minimizes the gasket heat leak and improves the thermal insulation integrity. Since there is only a small door opening, the internal space is never subjected to the significant warming from the environment that occurs from opening a conventional access door through which a human can reach. A further advantage of the cylindrical shape is that vacuum insulation may be more effectively applied because corners, where heat tends to enter regular rectangular cabinets, are minimized. The total heat leakage reduction is estimated at better than 40% for equivalent thermal insulation types. Once the thermal heat leakage has been minimized, the cooling equipment is the next area of focus. Here it is proposed that the free-piston Stirling cooling engine, also called a Stirling cooler, be used because it has demonstrated a factor of two in reduced energy consumption for the same thermal load as compared to conventional cascade systems. The combination of a circular, cabinet, a small access door and a free-piston Stirling cooler reduces the input energy to about 30% of that needed by a regular cascade cooled ULT freezer of similar interior volume. Since energy consumption is only a useful measure when compared on an energy usage per vial basis, it is necessary to obtain the highest packing factor of sample vials as is possible within the freezer cold space. This is achieved by storing the sample vials separately from the boxes usually used to organize them. The sample vials are preferably stored on circular, rotatable trays in close proximity to each other in order to maximize packing density.

The invention also is directed to the uniformity of internal temperatures. This is achieved by surrounding the interior volume with a two-phase thermosiphon connected to the free-piston Stirling cooler. Since the thermosiphon is isothermal and since the heat enters the cabinet through the walls only, the thermosiphon is able to intercept the incoming heat leak and create an isothermal barrier boundary around the sample vials stored within the ULT freezer thus essentially guaranteeing uniform temperature within the cold space. This is not possible in conventional ULT freezers because heat that enters through the gasket and door must exit through the interior cooled walls and so will set up temperature gradients within the cabinet space. Of course it is also not possible to actively cool the door interior surface so the use of the ultra small door into the cold space maximizes the interior wall area covered by the isothermal barrier area that intercepts the incoming heat leak.

The preferred embodiment of this invention also provides simple access to all parts for service when needed. To facilitate internal access, the top of the freezer is removable. This section contains the free-piston Stirling engine and all electronic controls. Once the top section has been removed, the internal parts may be accessed. This includes the carousel trays, the trolley and the stepper motors and drives that are subsequently described.

Figure 2:
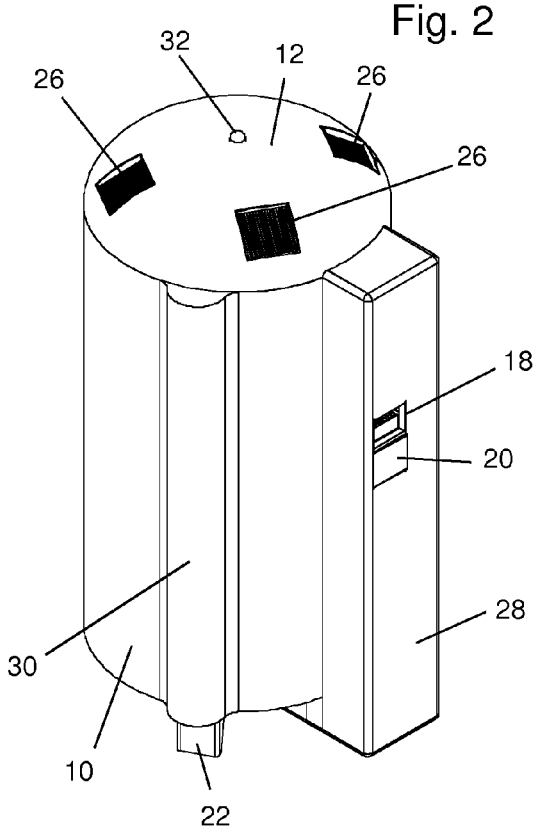
FIG. 2 is a view in perspective of a freezer embodying the invention.
Figure 3:
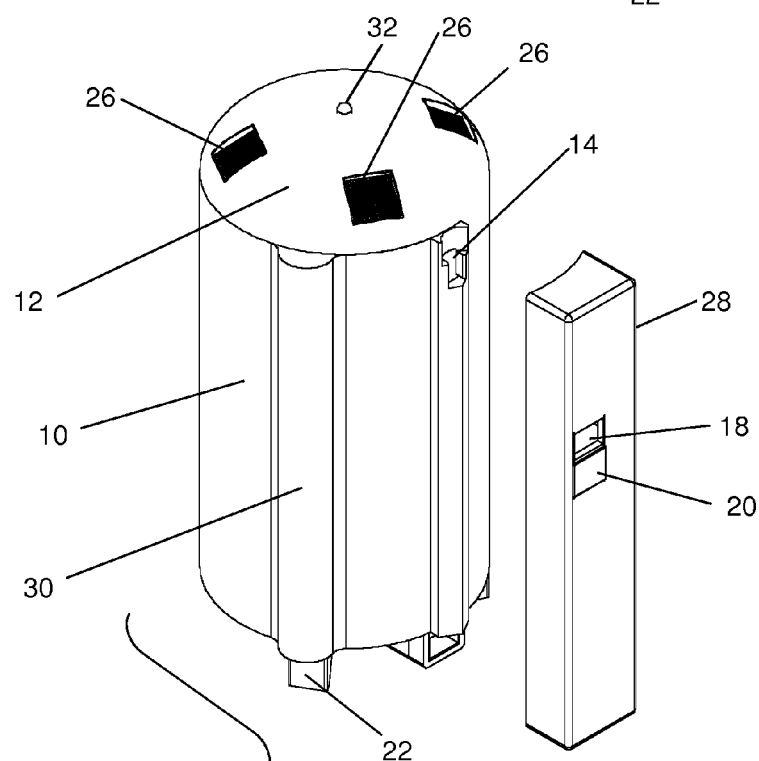
FIG. 3 is an exploded view in perspective of a freezer embodying the invention with its tray handler housing separated.

FIGS. 1 through 3 show the basic external views of an embodiment of the ULT freezer of the invention. The ULT freezer has a cylindrical side wall 10 so that it has a circular horizontal cross section in order to reduce the external surface area per unit of internal volume and by so doing, reduce the heat leak. The free-piston Stirling cooling system is mounted under the top dome 12 along with all the control electronics and the heat rejection system. There is no conventional door, only a small portal with an access door 14 that is opened when sample vials are ready to be received from or delivered to a user. The opening of the access door 14 of the portal can be arranged so that it will only open when a security tag or password is presented to the freezer.

Referring to FIGS. 1-6, the cylindrical freezer is vacuum panel insulated with polyurethane foam backing 16 as is typical for ultra-low temperature freezers. An access port 18 is where the sample vials are presented or retrieved by a person and is normally closed by door 20. Door 20 may be controlled by a pin code or presenting a security tag. Legs 22 support the freezer and may be bolted to the floor for stability during earthquake or tremor events. The top dome 12 is a lid that houses the free-piston Stirling cooling equipment 24 (FIGS. 4 and 5), its controls and its heat rejecting heat exchangers 26. The preferred Stirling cooler is a free-piston configuration. This configuration uses gas bearings for long life and high reliability, is modulatable so that the input may be adjusted to meet the heat lift required at the set cold temperature and is dynamically balanced so that casing vibrations are attenuated to very low residual levels. For equivalent thermal load, the use of free-piston Stirling technology reduces energy consumption by about 50% over conventional cascade equipment. Housing 28 holds a tray handling mechanism and is not part of the interior cold space of the freezer. Fairing 30, houses stepper motors that rotate internal carousel trays, which are subsequently described. An emergency identification light 32 to denote malfunction is placed at the top of the freezer. Plenum 34 covers a bottom access port 36 where dropped sample vials are automatically retrieved. The bottom port also serves as an outlet for water during deicing or decontamination.

The base 38 of the interior of the cold space (FIGS. 4 and 5) has a concave, preferably conical, surface with the access port 36 at its lowest point and with a removable or openable closure (door) 40 covering the opening. Vials that may be dropped within the freezer cabinet will roll to the opening and the door can be opened to allow the vial to fall out through the bottom access port 36 where it can be retrieved.

FIG. 7 shows the Stirling cooler 24 connected to a thermosiphon 42 that is connected to the cold head 44 of the Stirling cooler 24. The thermosiphon 42 has a tube that is wound around the internal cold space of the freezer. Inside of the tube is a two-phase (liquid and vapor) refrigerant at the operating temperature of the freezer, typically ethane or SUVA95, but other fluids with similar properties will also work. The refrigerant condenses at the outside surfaces of the cold head 44 of the Stirling cooler and evaporates as it intercepts the heat flowing through the insulation 16 into the cabinet essentially at isothermal conditions. The refrigerant never enters the Stirling cooler. The tubular thermosiphon 42 is preferably helically wound against or embedded within the inner surface of the cylindrical insulation 16. However, a rectangular step 46 is formed in each turn of the thermosiphon to provide an unobstructed vertical channel with the clearance that is necessary to accommodate vertical movement of a trolley, which is a component of the sample vial placement and retrieval robot to be subsequently described.

Figure 8:
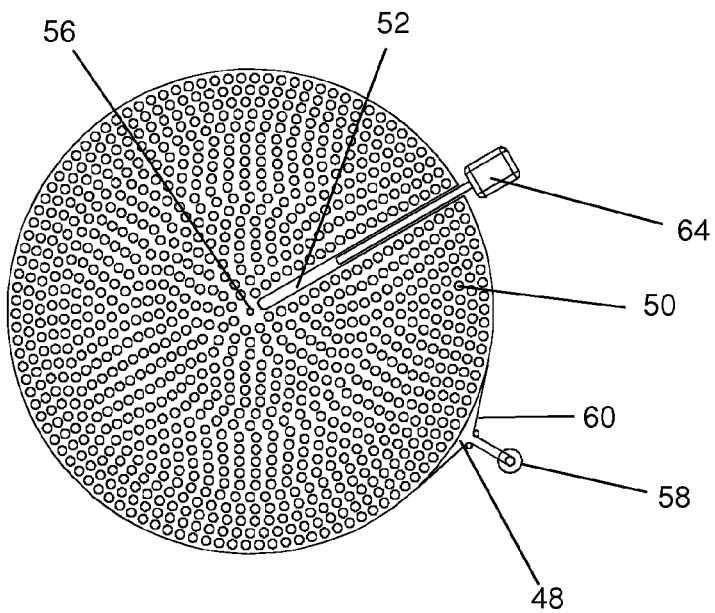
FIG. 8 is a top plan view of a tray containing sample vials and its rotational drive that are components of some embodiments of the invention.
Figure 9:
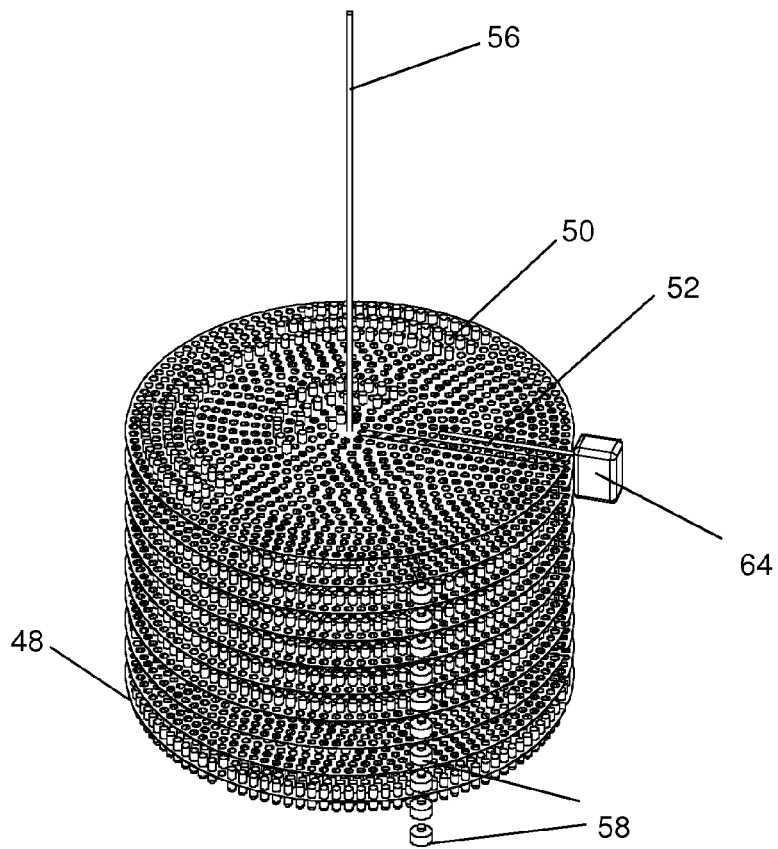
FIG. 9 is a view in perspective of some of the stacked trays and their drives that are components of some embodiments of the invention.

In order to arrange the sample vials within the cabinet so that selective access can be accommodated, a carousel system is used where the vials are stored independently of their boxes or trays. FIGS. 6, 8 and 9 show the basic structure of the carousel system. Some of the carousel trays have been removed from FIG. 8. Multiple, circular, coaxial, independently rotatable trays 48 are vertically stacked in the cold interior space extending upward from the base 38 to the top 54. Each tray 48 has a matrix of closely-spaced pockets, indents, a grate or other arrangement (referred to collectively as pockets) that provides a plurality of unique openings, each opening receiving one of the sample storage vials 50. The trays 48 are rotatable on a single spindle 56. Each of the trays 48 has a radial slot 52 which is an unobstructed radial opening extending radially inwardly from the outer periphery of each tray. In the rest position, when no access to vials is requested, the slots 52 are vertically aligned to provide an unobstructed vertical path extending from above the top tray to below the bottom tray. The slots 52 provide clearance so that a reach arm of the trolley robot can move vertically past the stacked trays as subsequently described. Together, the carousel system provides a three-dimensional matrix of closely spaced pockets for storing vials or other containers.

Each tray 48 of the stacked carousel is rotatably driven through a precise angle around the spindle 56 by individual controlled position motors 58. The prior art has long provided a variety of electric motors for which their position can be controlled, and therefore the position of a body, that is driven by such a motor, is controlled. These include servomotors, stepper motors and other systems using sensors and feedback control systems that have long been well known in the art. Preferred with this invention are stepper motors 58, each stepper motor driving one of the trays 48 through its own dedicated sprocket drive 60 (FIG. 8). Each sprocket drive 60 is fabricated from a material of low thermal conductivity, such as stainless steel or plastic, in order to minimize conduction of heat into the cabinet due to thermal conductivity of the sprocket chain and thereby presents negligible thermal load to the interior space. The sprocket drive may be a chain, belt or other flexible strand-type drive linkage and is preferably a chain or stainless steel ribbon. The term "drive chain" is used to refer collectively to them. Preferably, the drive gear on each motor 58 has sprocket teeth and the sprocket drive engages these teeth and surrounds a major angular portion of each tray but not the radial slots 52. The sprocket drive chain is not endless but instead has one end anchored to its tray on one side of the slot and the other end anchored to the tray on the opposite side of the slot. There is no need for sprocket teeth on the trays since the sprocket chain is anchored to the tray. Between its ends, the sprocket drive chain 60 drivingly extends around a sprocket on the stepper drive motor 58. The preferred chain is a chain having links that are simple closed loops, each link looping though it neighbors, similar to the chains commonly found on cuckoo clocks. Such chains allow minimal heat transfer because they have minimal metal to metal interfacing contact.

Unfortunately, the stepper drive motors 58 could be inhibited or disabled by the colder temperatures of a biological freezer. At these temperatures, the lubricant in the bearings gets more viscous, the bearings shrink from thermal contraction and the machine binds. However, the stepper motors 58 must be inside the freezer so they can be mechanically linked to drive the carousel trays 48. An important aspect of the invention is the placement of the stepper motors 58 in a warmer section of the freezer but doing so in a manner that neither interferes with the driving connection from the motors 58 to the trays 48 nor increases the conduction of heat into the interior or cold space of the freezer. Referring to FIGS. 1-3 and 6, the fairing 30 partially surrounds the exterior of a portion of the insulation 16 at which the stepper motors 58 are located. As seen in FIG. 6, each stepper motor 58 is located in a cavity 62 formed in the insulation 16. The cavity 62 can be a single vertically extending cavity along which all the stepper motors are spaced in a vertical arrangement or the cavity can comprise a vertically arranged series of small individual compartments, each compartment receiving a stepper motor 58. The cavity 62 is surrounded on all sides with insulation. Importantly, the tubes of the thermosiphon 42 are positioned interiorly of the cavity 62. The interior side of the cavity 62 also has an insulation wall 61 along the interior side of the cavity 62 to provide an insulative barrier between the cold interior of the freezer and the stepper motors 58.

FIG. 10 illustrates, in more detail, the stepper motors 58 within the vertical cavity 62 formed within the foam insulation 16. The tubes of the thermosiphon 42 are embedded in the walls of the insulation 16 and the stepper motors 58 are in staggered positions between the thermosiphon tubes so that their drive chains 60 pass between the thermosiphon tubes 42 and around at least a portion of the circular carousel trays. An insulation wall 61 is positioned along the interior side of the cavity 62 to complete the surrounding of the cavity 62 with insulation. Even a small or relatively thin wall of insulation on that side will allow the motors to run at higher temperatures. The insulation wall 61 has openings 59 for each sprocket drive chain 60. The openings 59 are only as large as needed to allow the sprocket drive chains 60 to pass through the openings 59 without interfering with their movement while they are rotating the trays 48 of the carousel.

FIG. 11 illustrates the temperature gradient from the exterior side wall 10 of the freezer to the thermosiphon 42. By positioning the stepper motors 58 within the cavity 62, the stepper motors 58 are located within the freezer where they can be drivingly linked to the trays 48 but they are also at a location in the cavity 62 where the temperature is warmer than within the freezer, as illustrated by the temperature gradient. Consequently, the stepper motors 58 are not inhibited or disabled by the colder temperatures (e.g. −86° C.) of the biological freezer.

Trolley Robot

FIGS. 12, 13, 16 and 17 illustrate a "trolley robot" 64 which is a vial placing and retrieving mechanism. The mechanism of the trolley robot 64 is shown in more detail in FIG. 12 with its cover removed from the main trolley robot housing. The trolley robot 64 is mounted on a carriage 65 that moves vertically on tracks 68. Stepper motors on the carriage 65 allow the trolley robot 64 to rotate about its vertical axis and also drive the carriage vertically on its tracks 68. In that manner, the trolley robot 64 indexes to a selected positional address having height, angle and radius coordinates. Height coordinates are applied to the trolley robot to drive it vertically to a height immediately above a tray 48 to access a vial in the tray. Radius coordinates are applied to the trolley robot 64 to drive its radially extending reach arm 66 to a selected radial position at a selected vial. Angle coordinates are not applied to the trolley but instead are applied to rotate the circular carousel trays 48. The reach arm 66 of the trolley robot 64 is retracted during storage.

A "garage" 70 (FIGS. 5 and 6) for the trolley robot 64 is located in a warmer section of the freezer. The garage 70 is positioned outwardly of the heat accepting evaporator, which is the thermosiphon 42, along the interior of the outer cabinet wall so it is at a relatively warmer temperature which is at least minus 40 degrees C. and F. Parking the trolley robot 64 in the garage 70 when not in use, allows it to function mechanically so it is not inhibited or disabled by colder temperatures partly for the same reasons described above that the stepper motors 58 could be disabled or bind. The garage 70 is described below in further detail.

The reach arm 66 operates in a manner similar to a retractable tape measure. A small stepper motor 72 (FIG. 12) controls the amount of extension of the reach arm 66. The stepper motor 72 drives pinion 73 that in turn drives main gear 75 winding the flexible reach arm 66 around its spindle that is attached to the main gear 75. An electrically activated picker 74 at the end of the reach arm 66 is able to magnetically attach or release itself to a target vial. When a vial is picked up by the reach arm 66, the reach arm 66 retracts until the vial is pulled against a nesting shelf 76 (FIGS. 12 and 18) for additional support during movement.

The trolley robot 64 has two attachment points 78, top and bottom, for connecting to the carriage 65 in the freezer cold space. A separate stepper motor 82 controls the vertical motion of the trolley robot 64 by moving the carriage 65 in a vertical direction along the track 68 in the vertical plenum 67 in the freezer cold space using a rack and pinion mechanism. Another stepper motor 84 rotates the trolley robot 64 by engaging sector gear 86. Whenever the trolley rotates, the extendible reach arm 66 is retracted to its rest position.

In FIGS. 5 and 6 the trolley robot 64 is shown in its garage 70 where it is sent by the control system when not required for accessing the sample vials. When the system goes into rest mode, that is when not activated to retrieve or store a vial, all the carousel trays rotate so that their slot or slots align vertically. When slots 52 are aligned, the trolley robot 64 is able to move unimpeded in a vertical motion up and down these slots spanning the entire stacked carousel structure. In the rest condition, the trolley robot 64 is parked at the highest part of its travel where the insulated garage 70 is located in order to allow the trolley to rest at warmer conditions in order to shelter its mechanism from extreme cold. When the freezer is commanded by freezer control software in the freezer control system to retrieve or store a vial, a carousel tray is rotated into position to allow the trolley robot reach arm 66 to reach and access the vial or place the vial in a pocket of a tray 48. Immediately thereafter, that carousel tray would rotate back to its rest position with the slots aligned and the trolley would be free to move to either retrieve a second vial for placement or moving the vial just retrieved to a mechanism for taking retrieved vials to an outermost, human accessible portal. Alternatively, the trolley robot 64 can return to its rest position in its insulated garage 70.

FIG. 14 shows the vial picker 74 on the end of the trolley reach arm 66. A small magnet 88 in a non-ferromagnetic picker casing 90 is solenoid actuated to pick up the vial. Referring to FIG. 15, the vial 92 has a corresponding ferromagnetic material or magnet 94 that is attracted to the magnet 88 and fixed to the cap 96 of the vial 92. To disengage the picker 74 from the vial 92, an electric current energizes a coil 98 (FIG. 14) of the solenoid on the picker 74 that lifts a ferromagnetic plunger 100 attached to the magnet 88 and moves it sufficiently far from the vial cap magnet 94 to disrupt the magnetic attraction between the picker and the vial and allow the vial 92 to drop into another support. A spring 102 returns the magnet 88 to its original position when the current through the coil 98 is switched off. An RFID, barcode or other tagging device 104 is attached to the vial 92, typically at the bottom but in the case of an RFID tag, it may be located anywhere on the vial body.

Garage and Portal Access Door

An important feature of the invention is the combination of the structure of the garage 70, its positioning in the freezer and its relationships to, as well as the size of, the portal access door 14. Referring principally to FIG. 5, the garage 70 for the trolley robot 64 is at the top of the vertical plenum 67 that is formed into the interior wall of the insulation 16. Preferably the garage 70 is also at the uppermost level of the interior of the freezer. The inward side of the garage 70 has a permanent insulated wall 106, although alternatively the garage can be formed with a larger recess that extends further upwardly so that the wall 106 can be shortened or even eliminated. A bottom insulated door 108 is horizontally oriented and can be opened and closed by a motor and/or movement of the trolley robot 64. The bottom insulated door 108 protects the trolley robot 64 from the deep storage temperatures within the freezer. This door 108 is opened automatically when the trolley robot needs to access a sample vial. As seen in FIG. 6, the vertical side walls of the plenum 67 also form side walls of the garage 70.

The portal access door 14 completes the enclosure of the garage 70 on all sides with thermal insulation. The door 14 slides vertically and is driven to its opened and closed positions by a drive motor (not shown). The door 14 is insulated and allows access to the interior space of the freezer through the intermediate function of the trolley robot 64. The door 14 is opened automatically by the control system for vial transfers into and out of the freezer. The size of the door 14 makes an important contribution to some of the improvements afforded by the invention. The door 14 must be sufficiently large to allow sufficient space for the trolley robot to deliver or retrieve a single sample vial to or from outside the freezer. However, this configuration permits the door 14 to be small enough to provide a substantial reduction of the heat transfer into the freezer and a more uniform temperature distribution within the freezer. The door 14 need only be large enough to pass the picker and a vial attached to the picker so the door can be extraordinarily small. The garage 70 must be sufficiently large in volume and dimensions to allow it to receive and house the trolley robot 64 including any vial or other container that the trolley robot 64 is moving in or out of the freezer and to allow the trolley robot 64 to rotate as described while supporting such a container. However, it is desirable that the garage 70 be no larger in volume and dimensions than necessary except to allow sufficient clearance to avoid striking the surrounding walls of the garage.

The door 14 is set at the highest point of the freezer cold space so that when it is opened, very little dense internal cold air falls by convection out of the freezer into the warmer room as is the case with conventional cabinet ULT freezers when the door is opened. The garage 70 is also positioned at the uppermost part of the freezer interior because the warmest air in the freezer is at the top and therefore this position assists the function of the garage in storing the inactive trolley robot at the warmest practical temperature. Additionally, as heat is conducted through the insulated door 14 into the garage 70 and from the garage 70 through the door 108 into the freezer, a temperature gradient exists from the door 14 to the interior of the freezer. That temperature gradient is like the temperature gradient illustrated in FIG. 11 and maintains the garage at an intermediate temperature, warmer than the temperature within the interior of the freezer.

The fact that the door 14 and its opening 18 into the interior of the freezer can be so small also provides additional advantages. Because a major source of heat conduction into the freezer is the gasket around the door, the smaller door means a smaller gasket and therefore less heat conduction into the freezer. Because a door can not have any thermosiphon tubes on or embedded in the interior surface of the door, the interior side of a door is always at a warmer temperature than the interior side of a fixed wall. The result of the temperature difference is a non-uniformity of the temperature distribution in the freezer. However, because the invention allows the door to be so small, the thermosiphon can occupy a greater proportion of the interior wall surface of the freezer, especially when compared to rectangular cabinets with doors. Therefore, the internal temperature distribution within the freezer can be considerably more uniform or homogeneous. A temperature difference from top to bottom of less than 3° C. is anticipated. It is believed that the cabinet and cooling equipment as configured in this invention will reduce energy consumption to about one third of the best conventional cascade cooled ULT cabinets at the same temperature and internal volume.

The preferred size of the access door 14 is about 40 mm wide by 100 mm tall. Depending on the size of the freezer, the area of the access door preferably should be less than 0.5% of the total internal surface area of the freezer. For small freezers of about 100 liter internal volume, the access door area according to this invention is more preferably about and not more than 0.3% of the internal surface area and about and not more than 0.1% for large 750 liter class freezers. Since heat gain to the internal space is dependent on the surface area of the freezer, the smaller the access opening, the smaller will be the thermal loss associated with the door and gaskets which, for current practice, accounts for about 40% of the thermal leak when door openings are included. In this invention, this heat gain is almost eliminated.

Tray Handling Mechanism

FIG. 3 shows the freezer separated from the housing 28 of a tray handling mechanism, referred to as a tray handler. The tray handler and its housing 28 is an independent assembly and may be removed from the freezer. The portal 14 in the freezer aligns with the tray handler in a manner that permits the reach arm 66 of the trolley robot 64 to access sample vials located in the tray handler when the trolley robot 64 has been rotated 180° from its position illustrated in FIGS. 8 and 9.

The tray handler 110 is shown in FIGS. 16-19 and is in its insulated housing 28 located externally of the freezer. Therefore, the tray handler 110 operates in a somewhat warmer environment thus imposing less stress on its moving parts. When a delivery (or receiving) tray 112 is placed through the human user access port 18, the tray 112 arrives at the base of the support frame 114 where the tray 112 is held in sliders 116. A tray may have any number of sample vials up to the maximum that can be placed into the tray. In the case of delivering vials to the freezer, a picker mechanism 118 moves down to lift the sample vials 120 out of the delivery tray 112 and brings them to the top of the support frame 114. The picker mechanism 118 moves on two screw jacks, one of which can be seen at 122. The screw jacks are driven by stepper motor 124 through gears at 126. One of the temporary storage trays, 128A through 128D, then moves along its sliders 130 into a position under the picker 118 and the picker 118 moves down again to place the sample vials 120 into the temporary storage tray that is presented under the picker 118. The temporary storage tray then moves back to its rest position as shown by 128B through 128D. Each storage tray 128A through 128D has its own stepper motor 132 to drive the storage tray back and forth using a rack and pinion or similar mechanism. Four such storage trays 128A through 128D are shown but the principle can be applied to as many trays as will practically fit into the space. The top temporary storage tray 128D is always filled first. For delivery, the mechanism works in reverse except that the picker 118 retains a first group of sample vials to deliver to the delivery tray 112.

Figure 17:
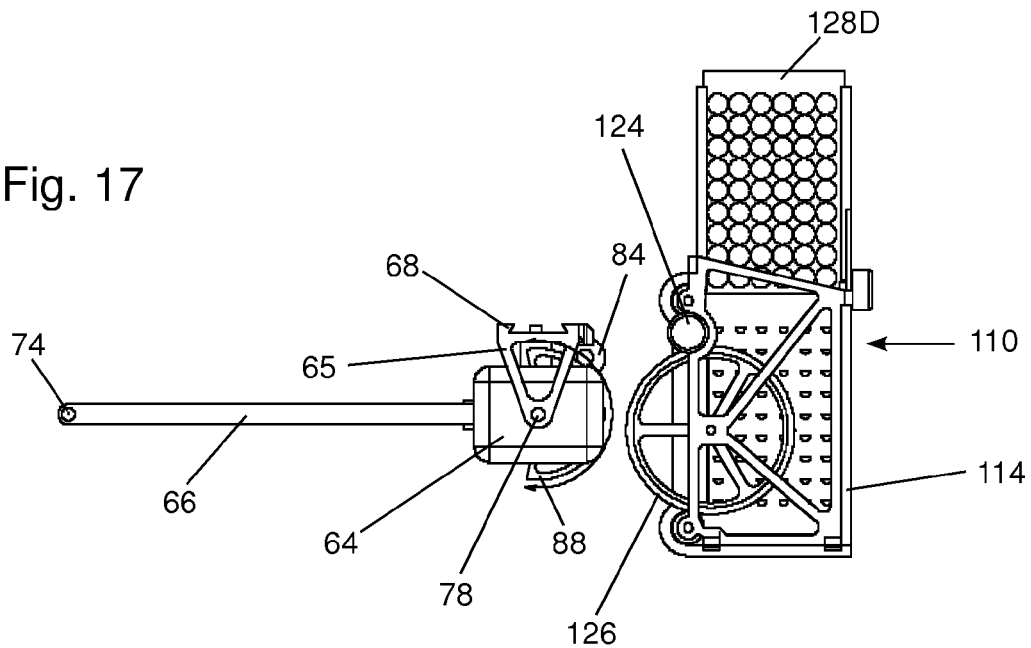
FIG. 17 is a top, plan view of a trolley robot and a tray handler embodying the invention for illustrating the cooperative relationship between them.
Figure 18:
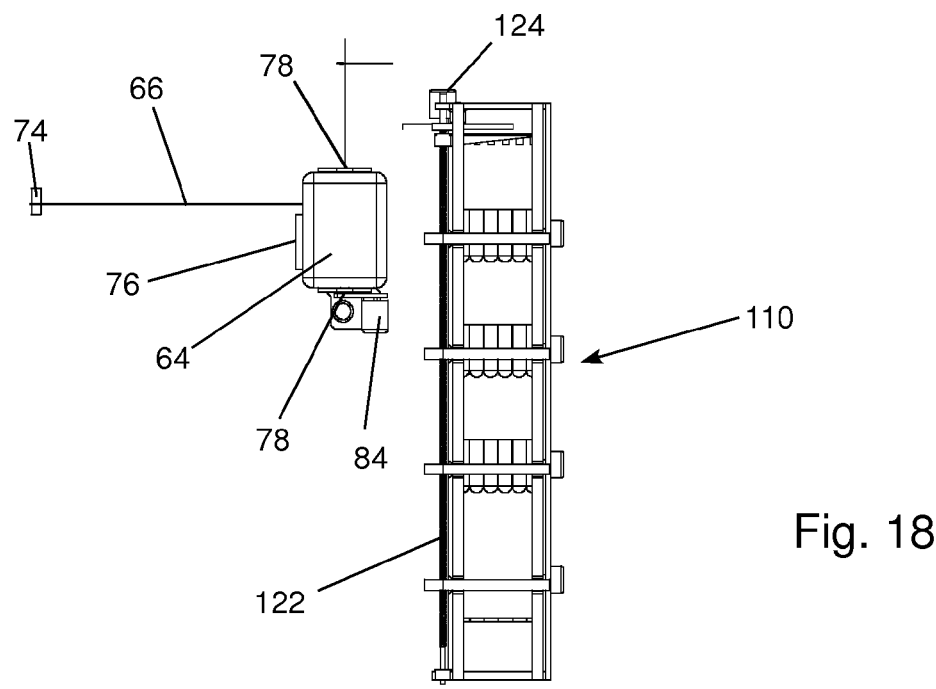
FIG. 18 is a view in side elevation of the trolley robot and tray handler of FIG. 17.

The orientation of the tray handler 110 and the trolley robot 64 are shown in plan and side views in FIGS. 17 and 18. The trolley robot 64 is, of course, located within its garage in the freezer interior space while the tray handling mechanism is located outside of the freezer interior space as previously described. When the vials have been placed into the temporary storage trays, the top tray 128D moves back under picker 118. This places the vials in reach of the trolley robot 64. The trolley robot 64 then retracts its reach arm 66, rotates on its carriage 65 so that it faces the tray handler 110 and extends its reach arm 66 radially outward from the trays to pick up a particular sample vial from the top tray 128D. Fine motion between the trolley reach arm 66 and the top temporary storage tray 128D allows access to any vial in the tray. The target vial is then lifted by the trolley picker 74, retracted against the trolley robot 64 and onto the trolley nesting shelf 76. The trolley robot 64 then rotates so that its reach arm 66 is directed radially inward of the freezer, moves vertically on its tracks 68 to position itself appropriately for delivery of the vial to a selected carousel tray 48 that has been rotated into position to present a storage pocket. Retrieval of sample vials reverses the process.

Once all the vials on the top temporary storage tray 128D have been moved into the freezer, the picker 118 returns to its parked position near the top as illustrated in FIG. 16 and a new tray is moved under the picker 118. The picker 118 lifts the vials from the new tray and moves to its top, parked position. The previously emptied top temporary storage tray 128D is then relocated under the picker 118. The picker 118 then deposits its vials into the top tray 128D and the process of moving the vial into the freezer is repeated. The mechanism works in reverse for retrieval of vials.

Figure 19:
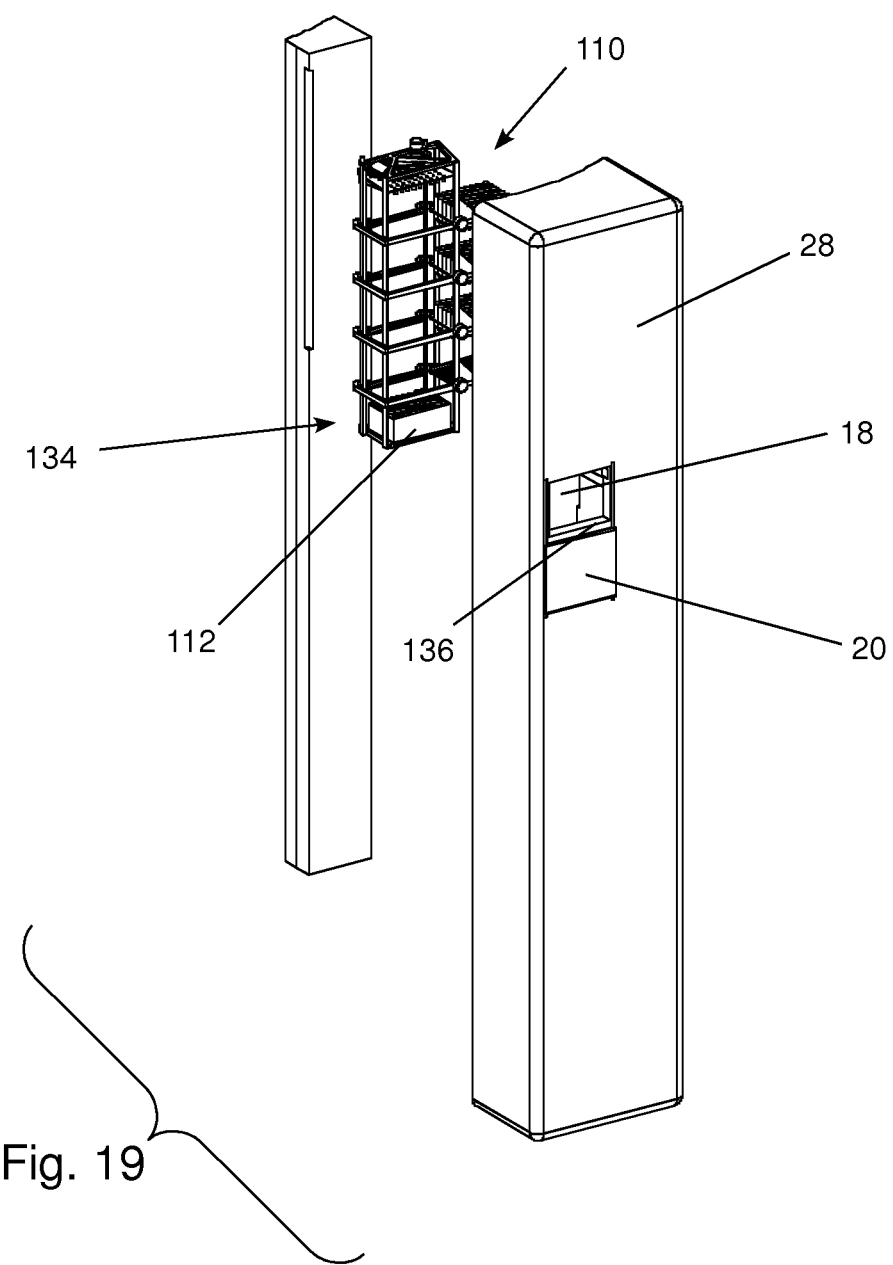
FIG. 19 is an exploded view in perspective of a tray handler and its housing.

Referring to FIG. 19, the tray handler 110 can be seen mounted within the insulated housing 28 and is positioned with its receiving/delivery section 134 (where delivery tray 112 is shown) aligned in registration with the user access port 18. Within access port 18 is a tag reader 136 so that any vial passed through the access port 18, retrieved or delivered, is tagged and recorded by computer software. If the tagging system is by barcode, then the reader is placed under the delivery tray in order to read the tags printed on the bottoms of the vials. If the tagging system is by RFID, then the reader may simply be in close proximity to the vials.

Colony of Freezers

Figure 20:
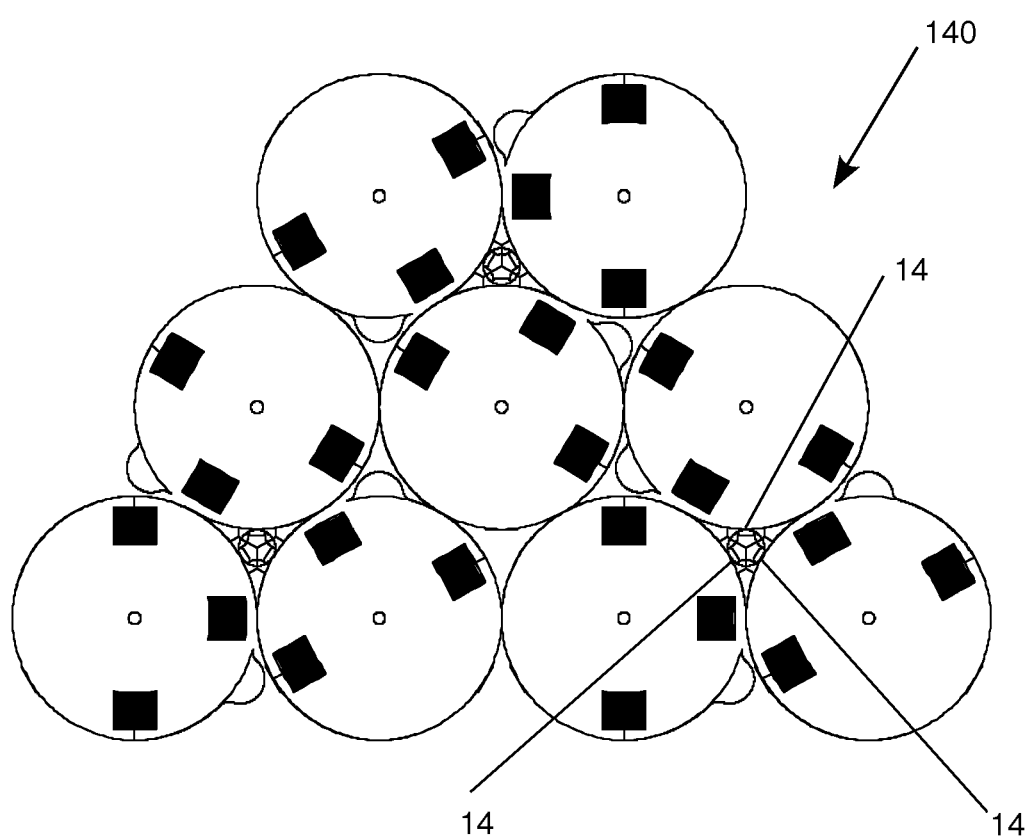
FIG. 20 is a top plan view of a colony of freezers.

Multiple ULT freezers are often placed near each other to offer additional cold space and backup in the event of mechanical failure. Since laboratory floor space is often expensive, using up as little space as is practical is advantageous. Additionally, multiple freezers are sometimes housed in large rooms for archival storage of tens of thousands of samples. FIG. 20 shows a plan view of how multiple freezers 140 may be stacked together to form a colony. The access ports 14 are aligned so that sample vials may be delivered to three freezer access ports simultaneously.

Figure 21:
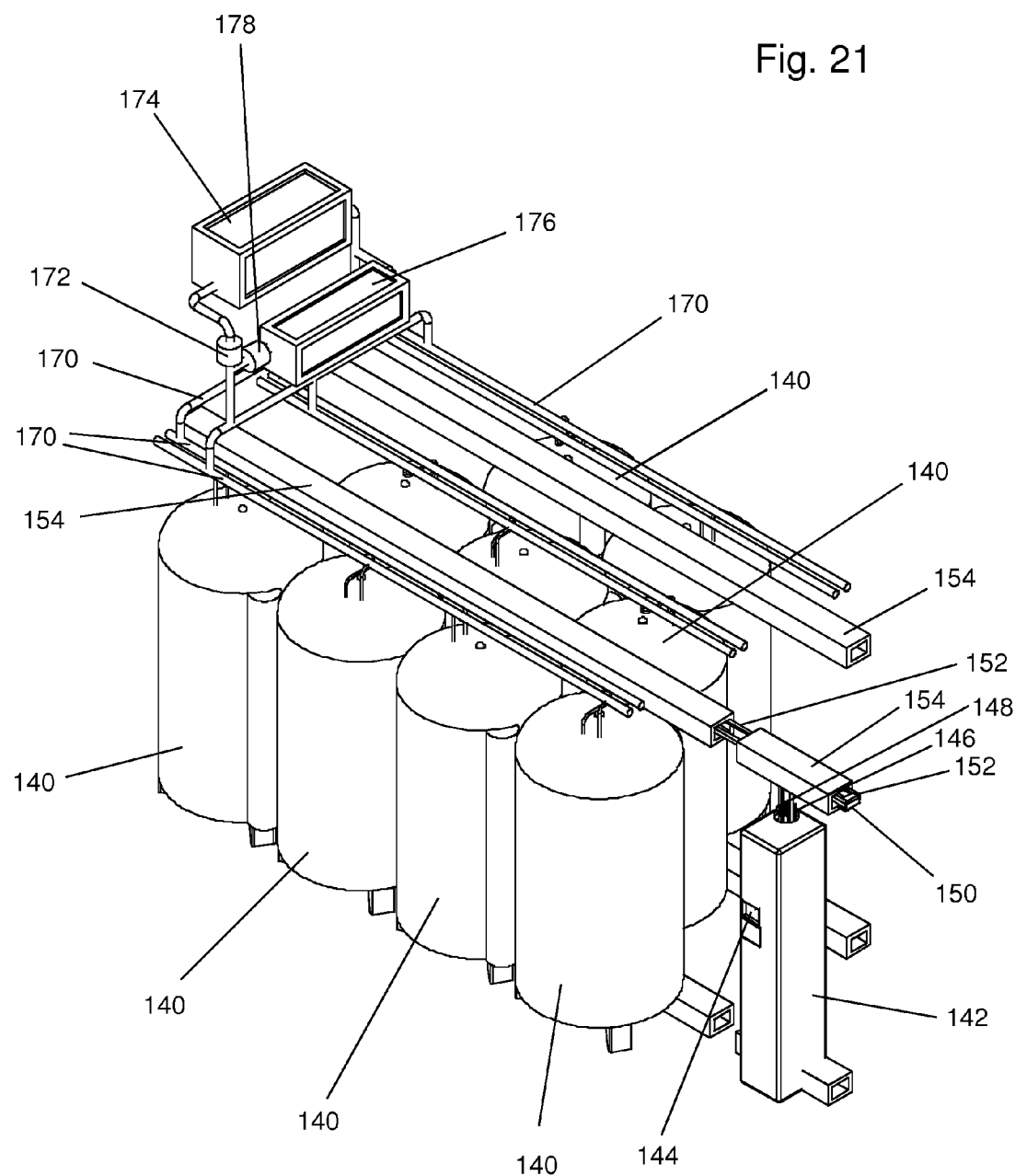
FIG. 21 is a view in perspective of the colony of freezers illustrated in FIG. 20 with vial handling apparatus and a combined, interconnected heat rejection apparatus for both maintaining the temperature in the freezers and simultaneously serving an HVAC function for maintaining the temperature in a room in which the freezers are operated.

By removing the tray handlers from each freezer, it is possible to close-pack groups of three freezer bodies in a single pack so that their access portals 14 align (only the access portals of one of the three groups are marked with reference numerals as a representative example). Each three-freezer pack can be close-packed with other three-freezer packs so packing efficiency is preserved. This advantage is only possible because the vial handling trolley robot has been placed within the freezer space. Vial access is handled differently in this situation as is shown in FIG. 21. A tray handler 142 is housed separately from the freezers and its operation is much the same as previously explained in connection with the tray handler of FIG. 16. A user access port 144 is now serviceable by multiple freezers. In this case, a special temporary storage tray 146 is able to move upwards on tracks 148 to a picker 150 moving on rails 152 within insulated channels 154. The picker 150 receives the vials from the temporary storage tray 146 and moves them to a three-freezer access point adjacent the access portals 14 of a three-freezer pack. At this point, another temporary storage tray moves up to receive the vials from the picker and returns to a position where the trolley robots can access the vials in the manner described before. For retrieval, the process works in reverse.

In this way multiple freezers can be placed as close together as possible in the form of a colony and by so doing, allow them to share sample vial storage space by passing vials between connected freezers. This allows vials to be automatically moved to another freezer if a problem arises with a particular freezer. This also facilitates auto defrosting and auto decontamination by automatically moving vials into a different freezer prior to defrosting or decontaminating the now empty freezer. Then when the defrosted or decontaminated freezer is back in operating condition and signals that it is ready to accept vials, the vials can be automatically returned.

Autodefrost and Autoclave

The prior art has shown a valved pipe inlet connected to a liquid $CO_2$ container for emergency cooling. The invention inserts a heater between the valve and the cabinet so that, for defrosting of the cabinet, the heater can be turned on to heat the $CO_2$ to a defrosting temperature. Alternatively, the $CO_2$ can be heated to 150 degrees or other appropriate temperature for autoclaving.

Referring to FIG. 4, an inlet pipe 160 is connected to a liquid $CO_2$ container and the inflow of $CO_2$ is controlled by a valve 162, as is typically employed in the prior art for ULT freezers in order to maintain temperatures when the power is disrupted or in some other emergency. However, with the invention, an electric, gas or other inline heater 164 is interposed between the valve 162 and the inlet pipe 160 to the freezer. The heater 164, if and when energized, raises the $CO_2$ temperature to levels sufficient to defrost or de-ice the interior space. In this case, the sample vials will have been removed before the use of heated $CO_2$ gas. Autoclaving by the use of a higher temperature $CO_2$ can also be implemented in this invention. Since the thermal insulation surrounding the freezer has high integrity, only small amounts of heated $CO_2$ will be needed to raise the internal temperature to de-icing or autoclaving temperatures. If the gas flow becomes excessive, it can be allowed to escape through a one-way valve pressure valve (not shown) and disposed of in a safe manner. Of course the heater 164 can alternatively be passive by not being heated in order to also permit conventional use of the $CO_2$ for emergency cooling, as in the prior art. For this purpose, the heater 164 has an electric switch or valve control 165 for turning the heater on or off. Defrosted water that condenses within a freezer can be extracted by gravity from the bottom opening 36.

Freezers as HVAC

By placing the freezers in close proximity as illustrated in FIGS. 20 and 21, it is possible to connect each freezer's heat rejection system to a single facility-wide heat rejection system and use the facility-wide system to not only take heat out of the freezers but also take heat out of the spaces in the facility that are occupied by facility personnel. In current prior art systems, heat that is conducted from the room into the freezer cabinet is transferred back into the room by the cooling engine, heat rejection system and then transferred in a second stage from the room to the exterior by the HVAC system.

The purpose of the refrigeration equipment, in this case a Stirling cooler but could be a conventional cascade system, for a freezer is to remove heat from the interior of the freezer that was conducted through its insulated walls or entered through the access door of the freezer when opened for access. The net quantity of heat transferred into the room from the freezers is the heat equivalent of the electrical energy coming in the power lines to operate the freezers. This is because the heat conducted into the freezer and heat pumped out of freezer by the refrigeration equipment balance to zero. So the net heat transferred into the room from the freezer is the heat from the electrical energy consumed by the refrigeration equipment.

In prior art freezer installations of the type having many freezers housed in a room of a building for storing tens of thousands of samples, that net heat is quite large. So large HVAC systems are used to remove the net heat that is being dissipated from the freezers into the room. The large HVAC systems consume a substantial quantity of electrical energy. As a result, prior art freezer installations that have large numbers of freezers incur the expense of purchasing, installing and operating two heat pumping systems, one to transfer heat from the freezers into the room and one to transfer heat from the room out of the building.

Figure 22:
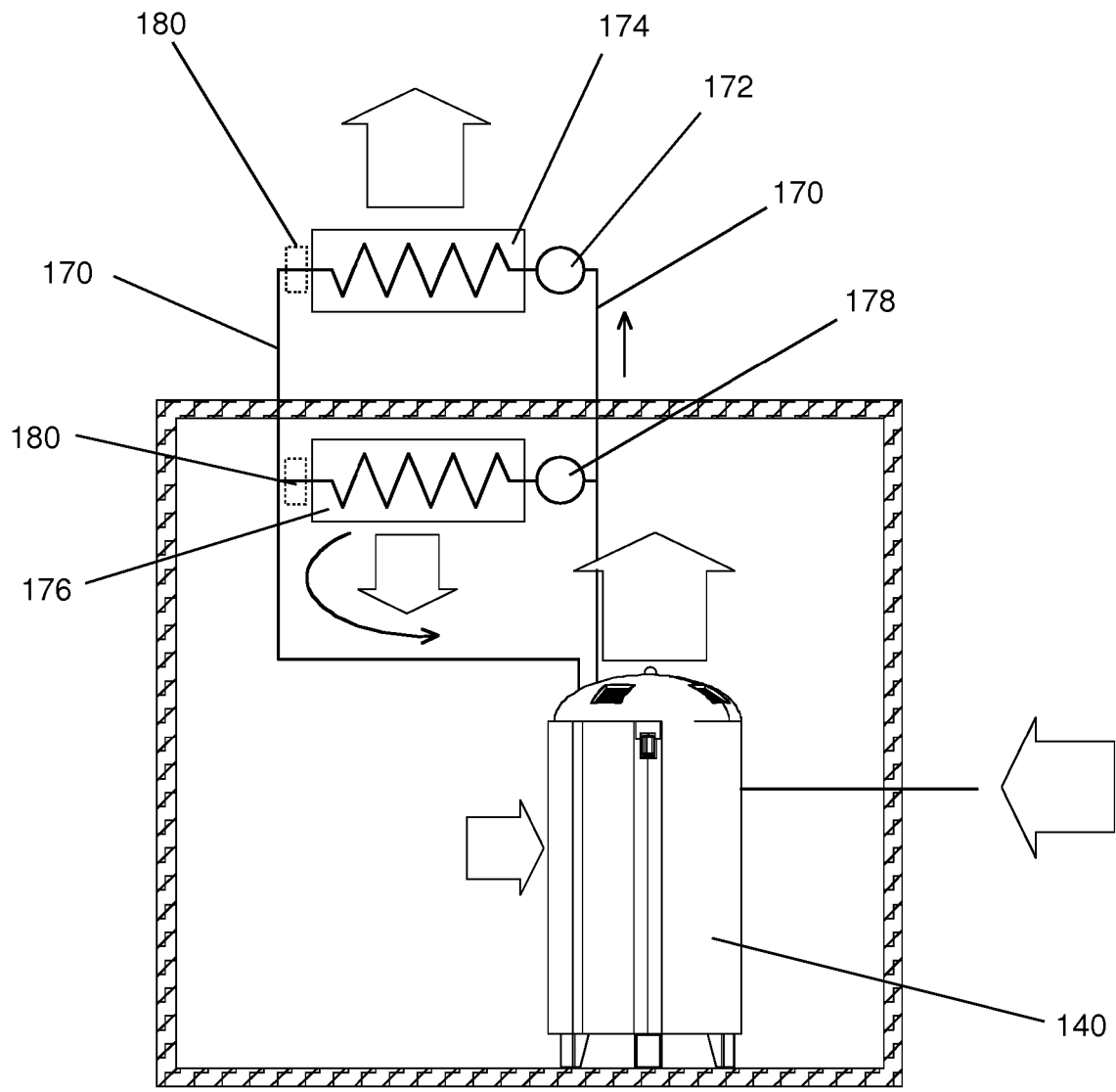
FIG. 22 is a schematic diagram illustrating the principles of the freezer colony and associated apparatus that are illustrated in FIG. 21.

FIG. 21 shows a pictorial view and FIG. 22 shows a diagrammatic view of a colony of freezers 140. Each freezer is actually functioning as a heat sink in its normal operation. Heat that is conducted into the interior of the freezer is pumped by the freezer's refrigeration system to a heat rejection system. For the invention, the heat rejection systems for multiple freezers have been unified into one shared or common heat rejection system. That common system is used to take heat out of the immediate space surrounding the freezers as a result of simultaneously taking heat out of the interior of the freezers and, in most weather conditions, reject the heat outside the building in which the freezers are housed. For example, the heat may be taken to the roof of the building thus removing all the heat that would otherwise have to be removed by the building HVAC system. In this case, operation of the freezers will extract heat from the building and thus additionally cool the space surrounding the freezers. At times, such as during the winter months, in order not to reduce the ambient temperature in the room too low, some heat can be returned back into the facility in order to maintain a comfortable temperature. By removing the heat from the facility in this manner, the system will be able to maintain any ambient set point temperature and therefore no facility HVAC would be needed.

This concept provides an additional energy reduction method that is available to the colony where the freezers' heat rejection systems are combined into one (or at least fewer) heat rejection system(s). Referring to FIGS. 21 and 22, a coolant liquid loop 170 (a system of fluid conveying pipes or tubes) forms a part of a heat rejection system that thermally links together all the heat rejection systems of each of the Stirling cooler refrigeration systems in each freezer. The coolant liquid loop 170 transports heat that is rejected from each freezer to one or more heat exchangers that are the final stage of the combined heat rejection system. Pump 172 moves the liquid through the heat rejection system and carries the rejected heat to an external heat exchanger 174 situated out of the immediate space housing the freezers, such as on the roof or on ground adjacent the building. A proportion of the heat rejected by the Stirling refrigeration system is transferred to one or more rooms of the building with an interior heat exchanger 176 and pump 178 so that the temperature can be maintained at a comfortable level without the need for a separate HVAC system. This system could save up to an additional 30% of the total electrical energy needed to operate the facility leading to a total energy consumption of about 23% or less of the energy that conventional freezer colonies currently consume. Operating power per freezer is also reduced by this arrangement because the heat rejection side runs cooler.

The relative proportions of heat dissipated outside the building and inside the building can be modulated by control of the flow rates of the coolant liquid through the heat exchangers 174 and 176. For example, adjustable valves 180 (FIG. 22) can be interposed in the coolant conveying pipes, the flow rates of the pumps 172 and 178 can be controllably adjusted using a thermostat control system, or both. A thermostat control system can vary the proportions of heat transported to the interior space and the exterior of the building to maintain a constant selected temperature in the interior space. The coolant can be a liquid coolant or alternatively a two-phase fluid to form a thermosiphon within the coolant conveying tubes. In summer, a higher proportion or all of the heat transported from the freezers is rejected outside the room so the room is "air conditioned" by the normal and usual transfer of ambient room heat into the freezers. In the winter, a smaller proportion of the heat transported from the freezers is rejected outside the room with the remaining proportion transferred back into the room. It is likely that the entire HVAC system can be eliminated, saving equipment, installation and operating cost. It is also likely that total energy cost would be less because heat transferred out of the room is done so by only one system.

Vial Management Database

Figure 23:
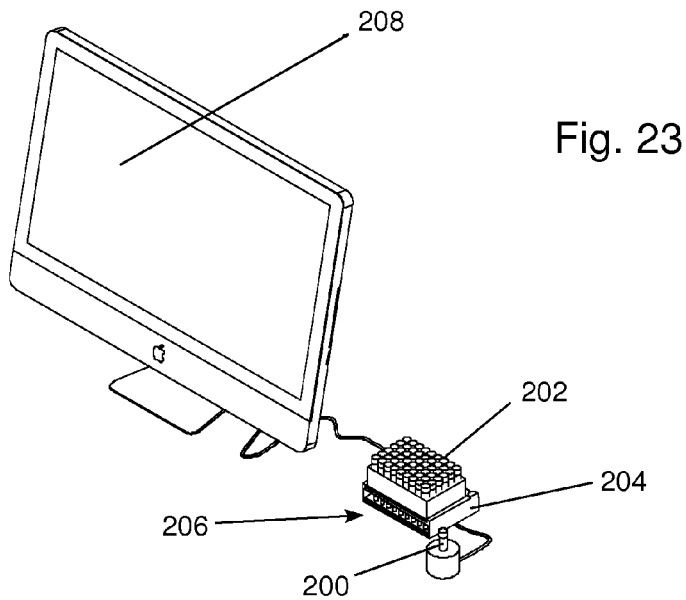
FIG. 23 is a view in perspective of a vial registration station and associated computer for maintaining a database that is used for control of the insertion and removal of vials from one or more freezers.
Figure 24:
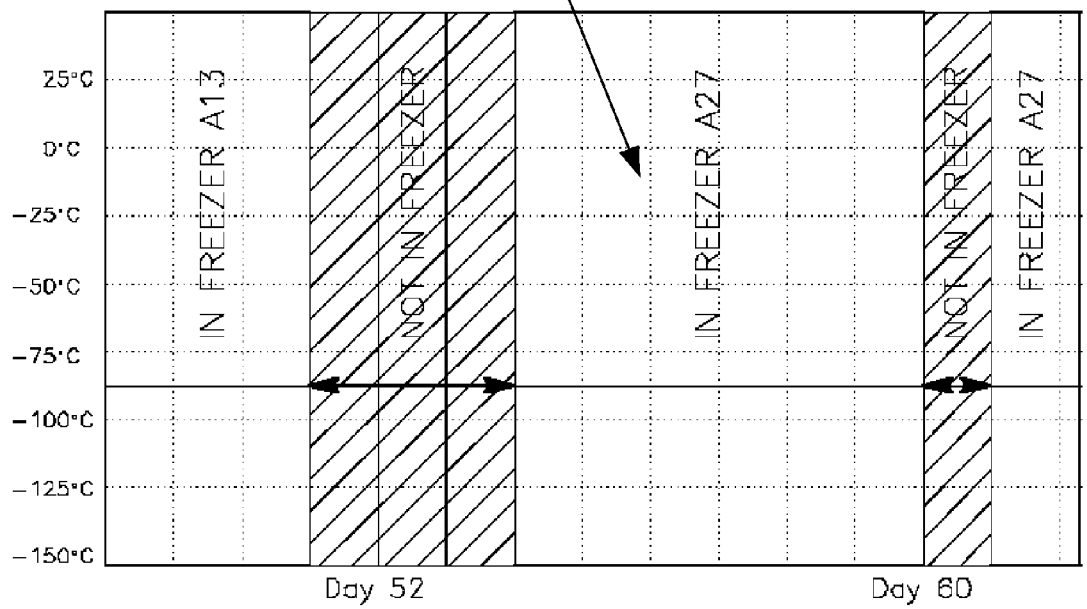
FIG. 24 is a chart illustrating the operation of the computer system and its database used to control the insertion and removal of vials from a freezer and to maintain a record of vials in the freezer and their location.

FIG. 23 shows a station where sample vials would be registered with the vial database software. The vials may be registered in any number up to the maximum allowable by the vial tray. Single vials may also be registered conveniently on a single sample vial registration table. FIG. 24 gives an impression of the sample vial management software user interface. In particular, temperature records are associated with the vials rather than the freezer.

Another part of this invention is the sample vial database that would, through communication with the ULT freezers, track the temperature and location history of individual vials. Because temperatures are now associated with the vials, there is no need to display the temperature of the freezer. Each freezer need only indicate malfunction and have an alarm beacon to identify a freezer that has malfunctioned. Freezer management would be the responsibility of the facility manager and not the researcher.

The freezer is designed to receive a single or multiple sample vials grouped in a tray that is placed on the receiving stage. When the vial tray is placed on the stage, a tag reader in the portal will read the tags attached to each sample vial and report the received vials to a database where the vials have been previously registered. The freezer vial management system will then instruct a robotic picker to move the vials from the vial tray to a staging location in the freezer where a second robot will remove each vial from the staging location for storage. Each sample vial will be registered to a storage location chosen by the freezer vial management system. When a user wishes to retrieve a number of vials, the freezer manager software will allow the user to specify the grouping of vials and these will be robotically selected from the freezer and moved to the staging area. The user will place a tray at the portal and the sample vials will be placed into the tray and presented at the portal for pickup.

In order for this system to work, the sample vials must be registered with a software database. This is done by placing the vials, either a single vial 200 or a tray 202 of any number of vials that can be placed in the pockets of a delivery tray 204, onto the registration station 206 as is shown in FIG. 23. The registration station 206 is connected to a computer 208 that records a unique identifying code for each vial that is then stored in a vial management database. The computer 208 is connected to the freezers through software so that the vial database can be accessed by the freezer system software. The freezers only accept registered vials. When the vials are presented to the main access port, the tag reader at the access port notes that particular vials have been delivered and allots specific pockets in the carousel trays to specific vials. The software system therefore knows where each registered vial is placed and is able to retrieve that specific vial when so requested. When a vial is retrieved, the main access port has another opportunity to check that the vial retrieved is indeed the correct one because the tag reader reads vials entering and exiting the portal. The software will access the vial database in a form as shown in FIG. 24. Items in the database may include:

a. A unique vial identifying number or code,
b. Vials grouping so that a tray of vials remains together,
c. Color or some other identifier for the user,
d. A chart signifier to interrogate the temperature history of a vial,
e. Location of current or last freezer that the vial is in or extracted from,
f. An alarm signaling either that the vial has been un-frozen for too long or is ready for retrieval or some other item demanding immediate attention,
g. A status entry to indicate the current condition of a vial sample.

Since the freezer stores and retrieves sample vials, it will need to associate each sample vial with a unique location within the freezer. It does this by tagging the sample vial either by bar code or preferably an RFID system and associates the storage place with that tag. The freezer then communicates to and notifies the computer 208 having the database resident on the computer 208 or on a server on the Internet, that it has the sample vial. When the sample vial is needed, the database software requests the sample vial and the freezer retrieves the vial and presents it to the portal for extraction.

Therefore, with the invention, computer firmware or software notes the uniquely tagged sample vial and an empty location on one of the rotating trays and through a control system instructs the trolley and the rotating tray with the empty location to accept the sample vial. For retrieval, the system works in reverse by receiving a message that a particular sample vial needs to be accessed, and knowing where that sample vial is located, presents it by rotating the appropriate tray to the access point for pickup by the trolley's reach arm. The control system works in a manner implied by the metaphor, random access memory.

REFERENCE NUMBER LIST 10 cylindrical side wall
12 top dome
14 small port (access door)
16 foam
18 access port
20 door
22 legs
24 Stirling cooler (electrically driven)
26 heat exchangers
28 housing for tray handler
30 fairing (houses stepper motors)
32 emergency ID light
34 plenum at bottom
36 bottom port
38 base (of interior)
40 bottom port door
42 thermosiphon (tube)
44 cold head of Stirling cooler
46 rectangular steps in thermosiphon
48 stacked rotatable trays
50 vials
52 radial slot in tray
54 top of interior
56 spindle for trays
58 stepper motors (for trays)
59 openings through insulation wall 61
60 sprocket drive
61 insulation wall at cavity 62
62 stepper motor cavity
Trolley
64 trolley robot
65 trolley carriage
66 reach arm of trolley robot
67 plenum for trolley tracks
68 trolley robot tracks
70 garage for trolley robot
72 stepper motor for trolley robot
73 pinion of stepper
74 picker
75 main gear of trolley
76 resting shelf to support vial when tape retracted
78 pivoting attachment points for trolley robot to its slider
80 slider of trolley robot
82 stepper motor cabin (vertical action of robot slider)
84 stepper motor to pivot trolley
86 sector gear engaged by stepper motor
Picker (74)
88 small magnet in picker
90 picker casing
92 vial
94 magnet on vial
96 vial cap
98 picker coil
100 picker solenoid plunger
102 spring of picker
104 tagging device on vial
106 garage interior wall
108 bottom door of garage
110 Tray handler
112 delivery tray
114 support frame
116 sliders
118 picker mechanism
120 sample vials
122 screw jack
124 stepper motor
126 gears (to stepper motor)
128A-128D temporary storage trays
130 horizontal slider
132 stepper motor for temp storage tray
134 receiving/delivery section
136 tag reader
Colony
140 freezers
142 tray handler (for colony)
144 user access port (colony)
146 temporary storage tray (colony)
148 sliders
150 picker 152 rails
154 insulated channels
Autoclave etc
160 inlet pipe from $CO_2$
162 valve
164 heater
165 valve or switch
166 inlet pipe to freezer
Freezer HVAC Function
170 coolant liquid loop
172 pumps
174 external heat exchanger
176 interior heat exchanger (internal)
178 pump (inside room)
180 adjustable valves
Vial Management Database
200 single vial
202 tray of vials
204 delivery tray
206 registration station
208 computer This detailed description in connection with the drawings is intended principally as a description of the presently preferred embodiments of the invention, and is not intended to represent the only form in which the present invention may be constructed or utilized. The description sets forth the designs, functions, means, and methods of implementing the invention in connection with the illustrated embodiments. It is to be understood, however, that the same or equivalent functions and features may be accomplished by different embodiments that are also intended to be encompassed within the spirit and scope of the invention and that various modifications may be adopted without departing from the invention or scope of the following claims.

The invention claimed is:

1. An ultra-low temperature freezer for operating at a temperature below −50 degrees C. and having an enclosed cabinet including a surrounding wall of thermal foam insulation having an interior side and an exterior side and a refrigerating apparatus, the freezer comprising:
   (a) a thermosiphon connected to the refrigerating apparatus and containing a two phase refrigerant, the thermosiphon comprising a tube wound in turns along the interior side of the thermal foam insulation;
   (b) a plurality of rotatable trays within the cabinet and inwardly of the thermosiphon for supporting contents stored in the freezer;
   (c) one or more cavities formed in and surrounded by the thermal foam insulation, the cavities being located exteriorly of the thermosiphon and interiorly of the exterior side of the thermal foam insulation at a location where the temperature is warmer than within the freezer and having a temperature gradient across the cavities; and
   (d) a plurality of tray drives, each drive including a controlled position motor mounted in one of said one or more cavities, each motor being drivingly linked to a rotatable tray for driving the tray in rotation to a selected angular displacement.

2. An ultra-low temperature freezer in accordance with claim 1 wherein each said cavity is surrounded on all sides with foam insulation and the motors are in staggered positions between turns of the thermosiphon tube and have drive chains passing through the foam insulation and between turns of the thermosiphon tube and around at least a portion of a carousel tray for driving the trays in rotation.

3. An ultra-low temperature freezer in accordance with claim 2 wherein each tray has a radial slot and the drive chain for each tray extends angularly around a portion of the tray from an anchored position on one side of the slot, around a sprocket attached to the motor that is drivingly linked to the tray and then around a further portion of the tray to an anchored position at the other side of the slot.

4. An ultra-low temperature freezer in accordance with claim 3 wherein the refrigerating apparatus is a free piston Stirling cycle cooling engine.

5. An ultra-low temperature freezer in accordance with claim 4 wherein the one or more cavities are a plurality of individual cavities, at least one said cavity for each motor.

6. An ultra-low temperature freezer in accordance with claim 3 and further comprising an access portal through the surrounding wall having a door as a closure for the portal, the access portal and its door having a surface area that is less than 0.5% of the total internal surface area of the freezer.

7. An ultra-low temperature freezer in accordance with claim 6 wherein the access portal and its door have a surface area that is less than 0.3% of the total internal surface area of the freezer.

8. An ultra-low temperature freezer in accordance with claim 7 wherein the access portal and its door have a surface area that is less than 0.1% of the total internal surface area of the freezer.

9. An ultra-low temperature freezer for operating at a temperature below −50 degrees C. and having an enclosed cabinet including a surrounding wall of thermal foam insulation having an interior side and an exterior side and a refrigerating apparatus, the freezer comprising:
   (a) a plurality of rotatable trays within the cabinet for supporting contents stored in the freezer and inwardly of a thermosiphon on the interior side of the thermal foam insulation;
   (b) a plurality of tray drives, each tray drive including a controlled position motor mounted in a cavity in and surrounded by the thermal foam insulation and located exteriorly of the thermosiphon and interiorly of the exterior side of the thermal foam insulation at a location where the temperature is warmer than within the freezer and having a temperature gradient across the cavities, each motor being drivingly linked to a rotatable tray for driving the tray in rotation to a selected angular displacement.

10. An ultra-low temperature freezer in accordance with claim 9 wherein the motors are in vertically staggered positions and each has a drive chain passing around at least a portion of a carousel tray for driving the trays in rotation.

11. An ultra-low temperature freezer in accordance with claim 10 wherein each tray has a radial slot and the drive chain for each tray extends angularly around a portion of the tray from an anchored position on one side of the slot, around a sprocket attached to the motor that is drivingly linked to the tray and then around a further portion of the tray to an anchored position at the other side of the slot.

12. An ultra-low temperature freezer in accordance with claim 11 wherein the refrigerating apparatus is a free piston Stirling cycle cooling engine.

* * * * *